US011358917B2

(12) United States Patent
Sharif et al.

(10) Patent No.: US 11,358,917 B2
(45) Date of Patent: Jun. 14, 2022

(54) SULFUR INJECTION IN FLUIDIZATION BED DEHYDROGENATION ON CHROMIUM CATALYST FOR DEHYDROGENATION PROCESS IMPROVEMENT AND PROCESS SCHEME OPTIMIZATION

(71) Applicant: SABIC Global Technologies B.V., Bergen op Zoom (NL)

(72) Inventors: Khaja Aliuddin Sharif, Riyadh (SA); Mohammed Bismillah Ansari, Riyadh (SA); Guillermo Leal, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 192 days.

(21) Appl. No.: 16/954,381

(22) PCT Filed: Dec. 12, 2018

(86) PCT No.: PCT/IB2018/059938
§ 371 (c)(1),
(2) Date: Jun. 16, 2020

(87) PCT Pub. No.: WO2019/123121
PCT Pub. Date: Jun. 27, 2019

(65) Prior Publication Data
US 2021/0078922 A1 Mar. 18, 2021

Related U.S. Application Data

(60) Provisional application No. 62/607,198, filed on Dec. 18, 2017.

(51) Int. Cl.
*C07C 5/00* (2006.01)
*C07C 5/333* (2006.01)
(Continued)

(52) U.S. Cl.
CPC .............. *C07C 5/3332* (2013.01); *B01J 8/24* (2013.01); *C07C 41/06* (2013.01); *C07C 11/09* (2013.01);
(Continued)

(58) Field of Classification Search
CPC ....... C07C 11/09; C07C 5/3337; C07C 11/02; C07C 41/06; C07C 5/3332; C07C 43/046;
(Continued)

(56) References Cited

U.S. PATENT DOCUMENTS 2,126,817 A 8/1938 Rosen
3,291,855 A 12/1966 Haensel
(Continued)

FOREIGN PATENT DOCUMENTS

CN 102910997 B 8/2014
CN 102911000 B 12/2014
(Continued)

OTHER PUBLICATIONS

Sattler et al. "Catalytic Dehydrogenation of Light Alkanes on Metals and Metal Oxides." *Chem. Rev.* 2014, 114 (2014) 10613-10653.
(Continued)

*Primary Examiner* — Sharon Pregler
(74) *Attorney, Agent, or Firm* — Norton Rose Fulbright US LLP

(57) ABSTRACT

Systems and processes for producing isomerized alkenes are disclosed. The systems mainly include an isomerization unit, a dehydrogenation unit, and a MTBE synthesis unit. A hydrocarbon stream is fed into the isomerization unit to form iso-alkanes in a sulfur free hydrocarbon stream. The sulfur free hydrocarbon stream is heated and then combined with a sulfur-containing hydrocarbon stream comprising sulfur containing compounds to form a reactant feed stream to the
(Continued)

dehydrogenation unit. The iso-alkanes is dehydrogenated to form iso-alkenes. The formed iso-alkenes comprising isobutylene can be used as a feed stock for the MTBE synthesis unit.

20 Claims, 6 Drawing Sheets

(51) Int. Cl.
*B01J 8/24* (2006.01)
*C07C 41/06* (2006.01)
*C07C 11/09* (2006.01)

(52) U.S. Cl.
CPC ...... *C07C 2521/04* (2013.01); *C07C 2523/26* (2013.01)

(58) Field of Classification Search
CPC ....... C07C 5/333; C07C 5/48; C07C 2523/26; C07C 2523/42; C07C 2521/04; C07C 2523/04; C07C 2523/14; C07C 2523/40; C07C 2529/06; C07C 5/321; C07C 5/3335; B01J 23/26; B01J 23/42; B01J 23/626; B01J 23/90; B01J 23/92; B01J 23/96; B01J 29/90; B01J 38/04; B01J 38/06; B01J 38/10; B01J 38/12; B01J 38/16; B01J 38/38; B01J 38/44
See application file for complete search history.

(56) References Cited

U.S. PATENT DOCUMENTS

| 3,708,550 | A | | 1/1973 | Beuther et al. |
| 3,937,746 | A | | 2/1976 | Croce et al. |
| 4,179,474 | A | | 12/1979 | Beuther et al. |
| 5,336,829 | A | * | 8/1994 | Boitiaux ................. B01J 29/90 |
| | | | | 585/659 |
| 2020/0239386 | A1 | * | 7/2020 | Benaskar ................ C07C 5/333 |

FOREIGN PATENT DOCUMENTS

| EP | 0568303 A2 | 11/1993 |
| WO | WO 93/01154 A1 | 1/1993 |

OTHER PUBLICATIONS

International Search Report and Written Opinion for PCT/IB2018/059938 dated Mar. 19, 2019, 11 pages.

* cited by examiner

SULFUR INJECTION IN FLUIDIZATION BED DEHYDROGENATION ON CHROMIUM CATALYST FOR DEHYDROGENATION PROCESS IMPROVEMENT AND PROCESS SCHEME OPTIMIZATION

CROSS REFERENCE TO RELATED APPLICATIONS

This application is a national phase application under 35 U.S.C. § 371 of International Application No. PCT/IB2018/059938 filed Dec. 12, 2018, which claims priority to U.S. Provisional Patent Application No. 62/607,198 filed Dec. 18, 2017. The entire contents of each of the above-referenced disclosures is specifically incorporated by reference herein without disclaimer.

FIELD OF INVENTION

The present invention generally relates to alkane dehydrogenation. More specifically, the present invention relates to systems and methods for alkane dehydrogenation using hydrocarbon streams that contains sulfur.

BACKGROUND OF THE INVENTION

Methyl tert-butyl ether (MTBE) is one of the most commonly used octane boosters for gasoline. Typically, MTBE is produced by reacting isobutylene with methanol in liquid phase. The isobutylene in this process can be formed by dehydrogenation of isobutane in the presence of a noble metal catalyst, such as chromium or platinum. As dehydrogenation of isobutane is highly endothermic, the catalyst is periodically heated to a high reaction temperature to provide reaction heat for the dehydrogenation of isobutane.

At a high reaction temperature, various side reactions and/or physical condensations can occur in the reactor, thereby forming carbonaceous deposits on the surface of the noble metal catalyst. These carbonaceous deposits, also known as coke, block the active sites of the catalyst, thus, significantly reducing the activity of the catalyst. In a conventional dehydrogenation unit, the deactivated catalyst is periodically regenerated by introducing air/fuel in the catalyst bed to combust the coke on the surface of the catalyst. Depending on the reaction conditions, the coke formation process is generally rapid such that the activity of the catalyst can drop below a desired level within a few minutes. Hence, frequent regeneration of catalyst is often required to maintain a consistent production rate of isobutylene. However, repeated catalyst regeneration under high temperature can greatly shorten the catalyst life. Replacing the noble metal catalyst can considerably increase the production cost for isobutylene.

Various continuous processes for the dehydrogenation of paraffinic and olefinic hydrocarbons have been described. By way of example, U.S. Pat. No. 5,336,829 to Boitiaux describes a continuous process for dehydrogenation of paraffinic and olefinic hydrocarbons with the addition of at least one sulfur compound before or simultaneously to the introduction of the charge into the dehydrogenation reactor using a series of moving bed reaction zones. In yet another example, Sattler et al. reviews catalytic dehydrogenation of light alkanes on metals and metal oxides in various reactor configurations (Chemical Reviews, 2014, 114, 10613-10653).

While various commercial processes have been described for dehydrogenation reaction, improvements in extending the life of the catalyst for alkane dehydrogenation are still desired. By way of example, in isobutane production a butamer drier can produce a pure stream, which is sulfur free. The drying process can include adsorbing sulfur-containing compounds on adsorbents. The drier can be regenerated by contacting the sulfur-rich adsorbent with isobutane forming a high-sulfur containing isobutane stream, which can affect the heat exchange material of construction of downstream unites (e.g., heat exchangers) leading to failure in longevity. This problem is usually resolved by combusting the high sulfur containing stream.

BRIEF SUMMARY OF THE INVENTION

A discovery has been made that provides a solution to the aforementioned deficiencies that are typically seen in processes involving alkane (e.g., isobutane) dehydrogenation in the presence of a catalyst. The solution is premised on a process that can improve catalyst life and time on-stream factor of a dehydrogenation unit by including a sulfur containing hydrocarbon stream into a fluidized bed for dehydrogenating isobutane. In particular, the rate of coke formation on the catalyst during the dehydrogenation process can be reduced, thereby increasing the reactor on-stream factor by 5 to 10 and reducing production costs for isobutylene. Notably, in some aspects of the invention, a sulfur-containing hydrocarbon stream feeding into the dehydrogenation reactor can bypass the heat exchanger and mix with a heated sulfur-free hydrocarbon stream to reach the reaction temperature, thereby avoiding the heat exchanger malfunction caused by a high sulfur level.

Embodiments of the invention include a process for producing isomerized alkenes. The process can include combining a sulfur-free hydrocarbon stream that includes iso-alkanes with a sulfur containing hydrocarbon stream that includes a sulfur-containing compound to form a reactant feed stream. In certain aspects, the temperature of the sulfur-free hydrocarbon stream is greater than the sulfur-containing hydrocarbon stream. The process can further include contacting the reactant feed stream with a dehydrogenation catalyst under conditions sufficient to produce a first product stream comprising iso-alkenes.

Embodiments of the invention can include processes for producing isobutylene. A process can include passing a sulfur-free hydrocarbon stream that includes isobutane through a heat exchanger to increase the temperature of the sulfur-free hydrocarbon stream. The heated sulfur-free hydrocarbon stream can be combined with a sulfur-containing hydrocarbon stream that includes a sulfur-containing compound and hydrocarbons to form a reactant feed stream. In certain aspects, the reactant feed stream can include isobutane and greater than 5 and up to 500 ppm of a sulfur-containing compound. In certain aspects, the temperature of the heated sulfur-free hydrocarbon stream can be greater than the sulfur containing hydrocarbon stream. The process can include contacting the reactant stream with a supported catalyst of Column 6 of the Periodic Table under conditions sufficient to produce a product stream that includes isobutylene.

Embodiments of the invention include a process for producing methyl tert-butyl ether. The process can include combining a sulfur-free hydrocarbon stream comprising isobutylene with a sulfur-containing hydrocarbon stream comprising isobutane and a sulfur-containing compound to form a reactant hydrocarbon stream. The sulfur-containing compound in the reactant hydrocarbon stream can be removed to form a desulfurized reactant hydrocarbon stream. The process can further include contacting the desulfurized reactant hydrocarbon stream with methanol to produce a second product stream comprising methyl tert-butyl ether and unreacted product stream comprising isobutylene and isobutane. The process can further include separating the unreacted product stream from the product stream. The process can further still include contacting the sulfur-containing unreacted product stream with a supported catalyst of Column 6 of the Period Table under conditions sufficient to convert the isobutane to isobutylene and produce an isobutylene product stream. During this process, the Column 6 catalytic metal can be converted from a metal oxide form to a sulfided form.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The term "time on-stream factor" as that term is used in the specification and/or claims means the fraction of time that a process unit and/or reactor is operating.

The use of the words "a" or "an" when used in conjunction with the term "comprising," "including," "containing," or "having" in the claims or the specification can mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification. With respect to the transitional phase "consisting essentially of," in one non-limiting aspect, a basic and novel characteristic of the process of the present invention are their abilities to dehydrogenate alkanes and inhibit the formation of coke.

In the context of the present invention, at least twenty embodiments are now described. Embodiment 1 is a process for producing isomerized alkenes. The process includes the steps of combining a sulfur-free hydrocarbon stream containing iso-alkanes with a sulfur-containing hydrocarbon stream containing a sulfur-containing compound and hydrocarbons to form a reactant feed stream, wherein the temperature of the sulfur-free hydrocarbon stream is greater than the sulfur-containing hydrocarbon stream; and contacting the reactant feed stream with a dehydrogenation catalyst under conditions sufficient to produce a first product stream containing iso-alkenes. Embodiment 2 is the process of embodiment 1, further including the step of passing the sulfur-free stream through a heat exchanger to increase the temperature of the sulfur-free hydrocarbon stream before combining the sulfur-free hydrocarbon stream with the sulfur containing hydrocarbon stream. Embodiment 3 is the process of any of embodiments 1 and 2, wherein the iso-alkanes include isobutane, and the iso-alkenes of the first product stream include isobutylene. Embodiment 4 is the process of any of embodiments 1 and 3, wherein the sulfur-free hydrocarbon stream and the sulfur containing hydrocarbon stream each contain n-butane, 1-butene, 2-butene, or a combinations thereof. Embodiment 5 is the process of any of embodiments 1 to 4, wherein the reactant feed stream contains isobutane and the sulfur-containing compound having a concentration of 5 ppm to 100 ppm, preferably 10 to 80 ppm. Embodiment 6 is the process of any of embodiments 1 to 5, wherein the hydrocarbons of sulfur containing hydrocarbon stream also contains isobutylene and/or isobutane. Embodiment 7 is the process of embodiment 6, further including the step of removing the sulfur-containing compounds from the sulfur containing hydrocarbon stream and the first product stream to form a desulfurized hydrocarbon stream and a desulfurized first product stream respectively; contacting, at least some of, the isobutylene of the desulfurized hydrocarbon stream and/or, at least some, isobutylene of the desulfurized first product stream with methanol to produce a second product stream containing methyl tert-butyl ether and an unreacted product stream containing isobutylene and isobutane; and recycling, at least some of, the unreacted product stream into the sulfur free hydrocarbon stream and/or reactant feed stream. Embodiment 8 is the process of any of embodiments 1 to 7, wherein the sulfur-free hydrocarbon stream is heated in a heat exchanger by a working fluid containing the product stream that contains iso-alkene. Embodiment 9 is the process of any of embodiments 1 to 8, wherein the sulfur containing hydrocarbon stream has a temperature in a range of 30° C. to 100° C., and the sulfur-free stream has a temperature in a range of 200° C. to 500° C. Embodiment 10 is the process of any of embodiments 1 to 9, wherein, in the reactant feed stream, the sulfur free stream has a sulfur content of less than 10 ppm, preferably less than 5 ppm. Embodiment 11 is the process of any of embodiments 1 to 10, the sulfur containing compound contains one or more organic sulfides, one or more organic disulfides, one or more organic polysulfides or combinations thereof. Embodiment is the process of embodiment 11, wherein the one or more sulfides have a formula of $R_1-(S)_n-R_2$, where n is 1 or 2, and $R_1$ and $R_2$ are each individually a hydrogen or an alkyl group. Embodiment 13 is the process of embodiment 11, wherein the one or more disulfides have a formula of $R_3-S-R_4-S-R_5$, where $R_3$ and $R_5$ are each individually a hydrogen atom or an alkyl group, and $R_4$ is an alkyl group bound to two sulfur atoms. Embodiment 14 is the process of any of embodiments 1 to 13, wherein the conditions sufficient to produce the first product stream include a reaction temperature in a range of 550° C. to 600° C., preferably about 580° C., and a reaction pressure of about 0.1 MPa. Embodiment 15 is the process of any of embodiments 1 to 14, wherein the conditions sufficient to produce the first product stream include a liquid hourly space velocity of 200 hr-1 to 300 hr-1, preferably about 250 hr-1. Embodiment 16 is the process of any of embodiments 1 to 15, wherein the process is performed in a continuous mode. Embodiment 17 is the process of any of embodiments 1 to 16, wherein the dehydrogenation catalyst include chromium oxide supported on alumina. Embodiment 18 is the process of embodiment 17, wherein the dehydrogenation catalyst is contained in a fluidized bed. Embodiment 19 is the process of any of embodiments 1 to 18, wherein the sulfur-containing hydrocarbon stream is formed by adding the sulfur-containing compounds into a $C_4$ stream flowed from a dryer.

Embodiment 20 is a process for producing isobutylene. This process includes the steps of (a) combing a sulfur-free hydrocarbon stream containing isobutylene with a sulfur-containing hydrocarbon stream containing isobutane and a sulfur-containing compound to produce a reactant hydrocarbon stream containing isobutylene and a sulfur-containing compound; (b) separating the isobutylene from the product stream; (c) contacting the isobutylene with methanol to produce a product stream containing methyl tert-butyl ether and unreacted product stream containing isobutylene and isobutane; and (d) contacting the unreacted product stream from step (c) with a supported Column 6 catalyst under conditions sufficient to convert the isobutane to isobutylene and produce an isobutylene product stream.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments can be combined with features from other embodiments. For example, features from one embodiment can be combined with features from any of the other embodiments. In further embodiments, additional features can be added to the specific embodiments described herein.

BRIEF DESCRIPTION OF THE DRAWINGS

For a more complete understanding, reference is now made to the following descriptions taken in conjunction with the accompanying drawings.

DETAILED DESCRIPTION OF THE INVENTION

The currently available method for dehydrogenating alkanes (e.g., isobutane) suffers a few deficiencies such as low production efficiency, short catalyst life, high coke production, and heat exchanger malfunction that can be caused by high sulfur content in the stream flowing there through. The present invention provides a solution to at least some of these problems. The solution is premised on a process for producing isomerized alkenes (e.g., isobutylene). By feeding a sulfur containing hydrocarbon stream to an alkane dehydrogenation reactor, the coke formation rate on the catalyst, which can include chromium, can be reduced. Therefore, the catalyst/dehydrogenation reactor can have a longer on-stream time in each on stream-regeneration cycle compared to a process with no sulfur-containing compound introduced in the dehydrogenation catalyst (non-sulfur containing process). Overall, the time on-stream factor for the dehydrogenation reactor can increase by 10 to 40 and the yield of isomerized alkenes can increase about 4% compared to non-sulfur containing process. Additionally, the method avoids passing hydrocarbon stream of high sulfur content through the heat exchanger located upstream to the dehydrogenation reactor, thus preventing the heat exchanger malfunction caused by high sulfur content.

These and other non-limiting aspects of the present invention are discussed in further detail in the following sections with reference to FIGS. 1 to 3.

Figure 1:
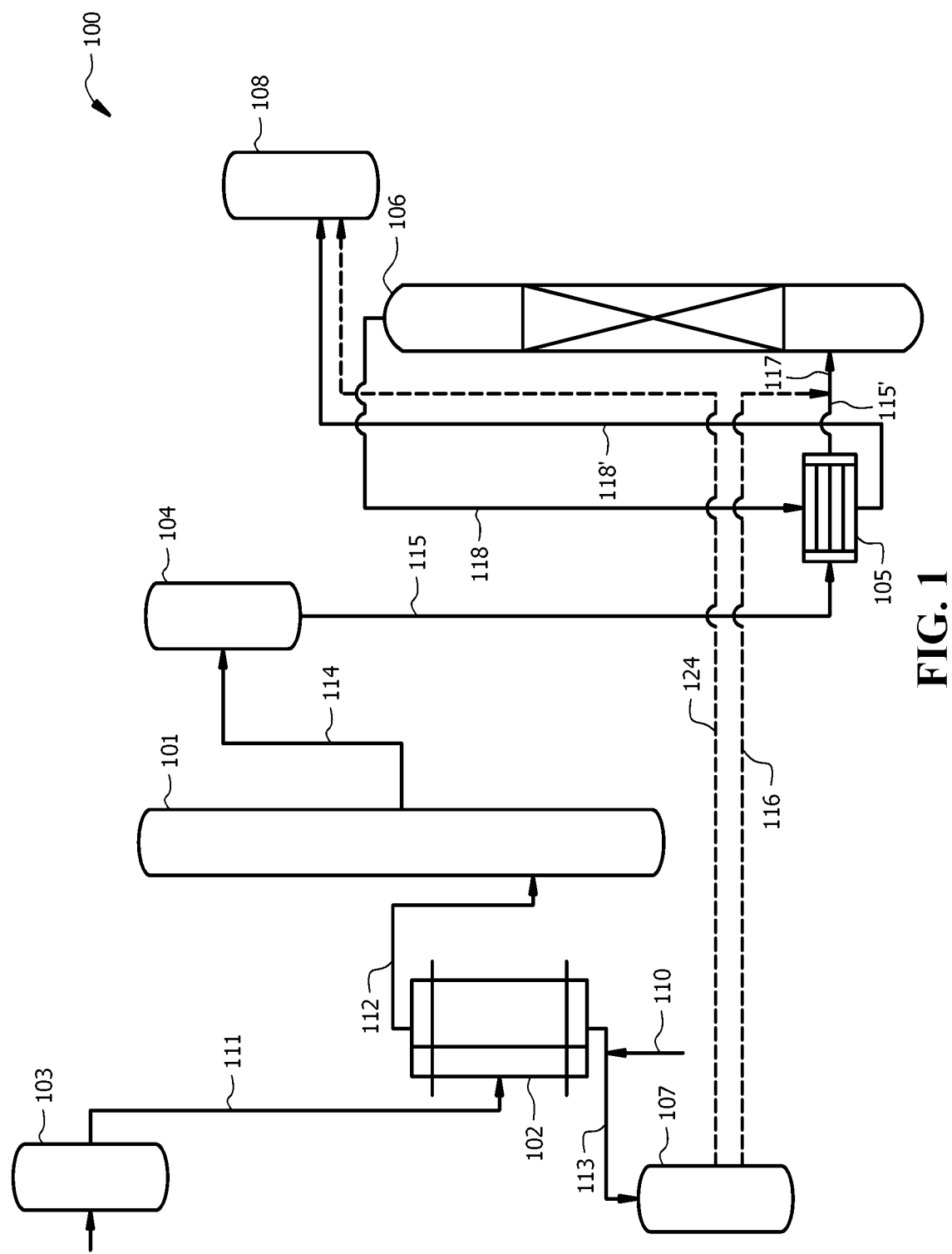
FIG. 1 shows a schematic diagram of a system for producing isomerized alkenes, according to embodiments of the invention.

FIG. 1 depicts a schematic diagram of system 100 for producing isomerized alkenes, according to embodiments of the invention. System 100 can include isomerization unit 101, dryer 102, feed vessel 103, feed vessel 104, heat exchanger 105, dehydrogenation reactor 106, and isobutylene storage unit 108. Isomerization unit is capable of isomerizing one or more n-alkanes to form one or more iso-alkanes. In certain aspects, isomerization unit 101 can include one or more fixed bed reactors. When more than one fixed bed reactor is used, they can be operated in series. Fixed beds in the fixed bed reactors can include an isomerization catalyst. Non-limiting examples of isomerization catalysts include platinum, palladium/$SO_4^{2-}$—$ZrO_2$, $H_3PW_{12}O_{40}$, aluminosilicate zeolite, or combinations thereof. In certain aspects, the isomerization catalyst can be supported on chlorinated-alumina.

To prevent formation of hydrochloric acid in isomerization unit 101, isomerization feed stream 112 contains no, or substantially no, water. Therefore, according to embodiments of the invention, an inlet of isomerization unit 101 can be in fluid communication with a first outlet of dryer 102. In certain aspects, dryer 102 can be configured to receive dryer feed stream 111 and strip water there from. Dryer feed stream 111 can include one or more hydrocarbons. In other more particular embodiments, the one or more hydrocarbons included in dryer feed stream 111 can include $C_4$ hydrocarbons. Dryer feed stream 111 can flow from feed vessel 103 to dryer 102. Non-limiting examples of isomerization unit 101 include a BUTAMER™ isomerization unit (UOP LLC, United States of America). Dryer feed stream 111 can include n-butane, and dryer 102 can be a BUTAMER™ dryer. The BUTAMER™ isomerization unit generally includes two fixed bed reactors operated in series.

According to embodiments of the invention, isomerization unit 101 can be adapted to receive at least some dried hydrocarbon contained in sulfur free stream 112 from a first outlet of dryer 102. In some embodiments, an outlet of isomerization unit 101 can be in fluid communication with dehydrogenation feed vessel 104 configured to receive stream 114 comprising iso-alkanes from isomerization unit 101. Dehydrogenation feed vessel 104 can be in fluid communication with heat exchanger 105, which is adapted to heat sulfur free hydrocarbon stream 115 flowing from dehydrogenation feed vessel 104. An outlet of heat exchanger 105 can be in fluid communication with an inlet of dehydrogenation unit 106. Heated sulfur free hydrocarbon stream 115' can exit heat exchanger 105 and enter dehydrogenation unit 106.

Dryer 102 can be in fluid communication with storage vessel 107, which is configured to receive at least some dried hydrocarbon of dryer feed stream 111. In some aspects, one or more sulfur containing compounds in stream 110 can be injected in hydrocarbons flowing from the second outlet of dryer 102 to storage vessel 105 to form sulfur rich stream 113. In some embodiments, dryer 102 is not necessary. By way of example, a splitter can be used to split stream 111 into sulfur free stream 112 and sulfur containing stream 111 when one or more sulfur containing compounds in stream 110 can be injected in stream 111 flowing from the splitter. In certain aspects, the sulfur containing-compounds can include one or more organic sulfides, one or more organic disulfides, one or more organic polysulfides, or combinations thereof. In some embodiments, the organic sulfides can have a formula of $R_1$—$(S)_n$—$R_2$, where n is 1 or 2, and $R_1$ and $R_2$ are each individually a hydrogen atom or an alkyl group. The organic disulfides can have a formula of $R_3$—S—$R_4$—S—$R_5$, where $R_3$ and $R_5$ are each individually a hydrogen atom or an alkyl group, and $R_4$ is an alkyl group bound to two sulfur atoms. First sulfur-containing hydrocarbon stream 116 from storage vessel 107 can be configured to join heated sulfur free hydrocarbon stream 115' to form reactant feed stream 117.

Dehydrogenation unit 106 can be configured to dehydrogenate, at least some, iso-alkanes contained in reactant feed stream 117 to form iso-alkenes. In certain aspects, dehydrogenation unit 106 can include one or more fluidized bed reactors and a catalyst regenerator. Catalyst from the one or more fluidized bed reactors can be continuously transported to the catalyst regenerator, configured to regenerate the catalyst by combusting the coke formed on the catalyst and restoring the heat required for dehydrogenating alkanes. The regenerated catalyst can be continuously transported back to the one or more fluidized bed reactors. The one or more fluidized bed can include a supported catalyst that includes a catalytic transition metal of Column 3-12 the Periodic Table. Non-limiting examples of transition metals include chromium (Cr), molybdenum (Mo), tungsten (W), ruthenium (Ru), palladium (Pd), platinum (Pt) and the like. In certain aspects, non-limiting examples of the supported catalyst can include an alumina supported chromium catalyst, and an alumina supported platinum catalyst. In a particular embodiment, dehydrogenation unit 106 is one fluidized bed reactor.

In certain aspects, iso-alkanes in reactant feed stream 117 can include isobutane. Dehydrogenation unit 106 is configured to dehydrogenate, at least some, isobutane to form isobutylene in first product stream 118. In some more particular embodiments, heat exchanger 105 can be a gas-gas exchanger. Heat exchanger 105 can be configured to use first product stream 118 as working fluid to heat sulfur free hydrocarbon stream 115 to form heated sulfur free hydrocarbon stream 115' and cool first product stream 118 to form cooled first product stream 118'. A work fluid outlet of heat exchanger 105 can be in fluid communication with isobutylene storage vessel 108, which is configured to receive cooled first product stream 118' from heat exchanger 105.

Figure 2:
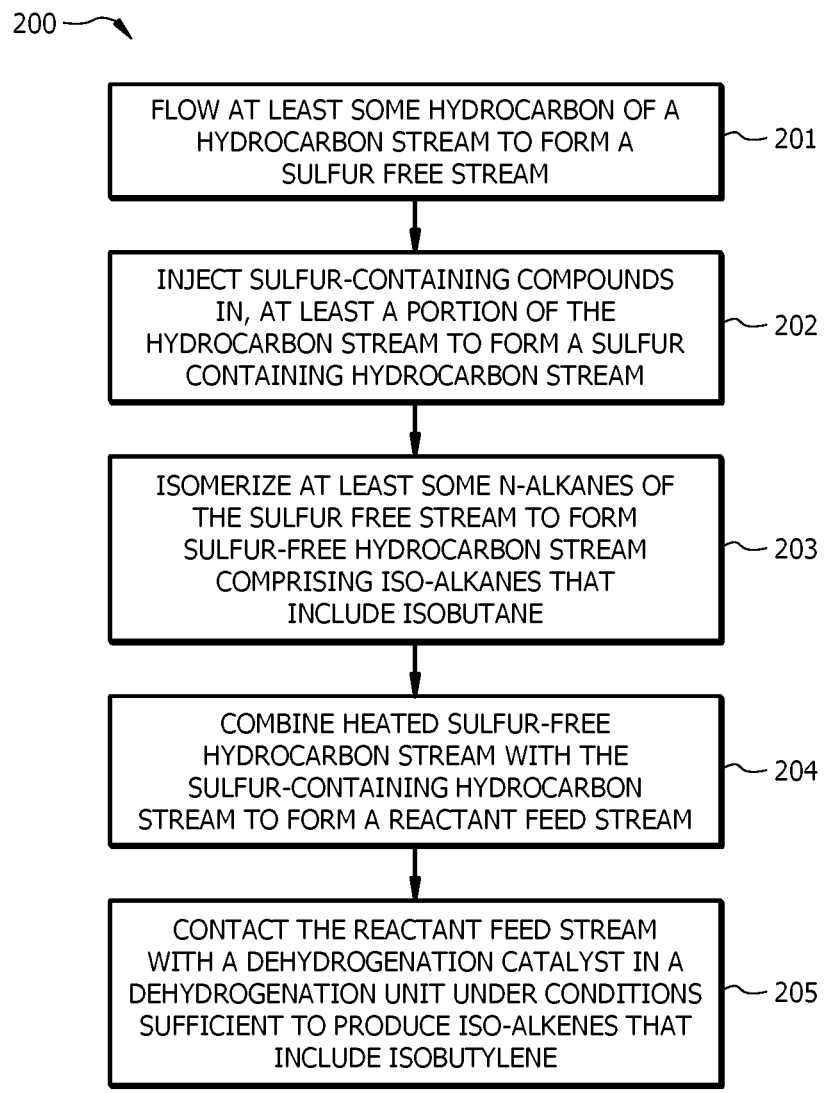
FIG. 2 shows a schematic flowchart for producing isobutylene, according to embodiments of the invention.

FIG. 2 shows process 200 for producing isomerized alkenes. Process 200 can be implemented by system 100 for producing isomerized alkenes, as shown in FIG. 1. According to embodiments of the invention, process 200 can include flowing at least some hydrocarbon from hydrocarbon stream 111 to form sulfur free stream 112, as shown at block 201. In certain aspects, hydrocarbon stream 111 can be a $C_4$ stream that contains primarily $C_4$ hydrocarbons. Non-limiting examples of $C_4$ hydrocarbon can include n-butane, isobutane, isobutylene, 1-butene, 2-butene, butadiene, and combinations thereof. Process 200 can further include injecting sulfur-containing compounds in at least some hydrocarbons of hydrocarbon stream 111 to form sulfur rich stream 113, as shown in block 202. In certain aspects, sulfur rich stream 113 can contain from 100 ppm to 5000 ppm sulfur-containing compounds, or greater than, equal to, or between any two of 100, 150, 200, 250, 300, 350, 400, 450, 500, 550, 600, 650, 700, 750, 800, 850, 900, 950, 1000, 1050, 1100, 1150, 1200, 1250, 1300, 1400, 1500, 1600, 1700, 1800, 1900, 2000, 2500 3000, 3500, 4000, 4500 and 5000. As described above, the sulfur containing-compounds can include one or more organic sulfides, one or more organic disulfides, one or more organic polysulfides, or combinations thereof. In some embodiments, the organic sulfides have a formula of $R_1$—$(S)_n$—$R_2$, where n is 1 or 2, and $R_1$ and $R_2$ are each individually a hydrogen atom or an alkyl group. The organic disulfides can have a formula of $R_3$—S—$R_4$—S—$R_5$, where $R_3$ and $R_5$ are each individually a hydrogen atom or an alkyl group, and $R_4$ is an alkyl group bound to two sulfur atoms.

In some more particular embodiments, hydrocarbon stream 111 can flow into dryer 102. At least some dried hydrocarbons from dryer 102 can form sulfur free stream 102. Sulfur-containing compounds can be injected to at least some dried hydrocarbons from dryer 102 to form sulfur rich stream 113, which can enter storage vessel 107. In certain aspects, hydrocarbon stream 111 can include primarily n-butane. Hydrocarbon stream 111 can further include isobutane and/or isobutylene.

As shown in block 203, process 200 can further include isomerizing at least some n-alkanes of sulfur free stream 112 in isomerization unit 101 to form stream 114 comprising iso-alkanes. In some more particular embodiments, the n-butane of sulfur free stream 112 in isomerization unit 101 is isomerized in isomerization unit 101 to form isobutane contained in stream 114. Stream 114 can be flowed into dehydrogenation feed vessel 104.

According to embodiments of the invention, sulfur-free hydrocarbon stream 115 that includes iso-alkanes enter heat exchanger 105 from dehydrogenation feed vessel 104. Sulfur-free hydrocarbon stream 115 can be heated to form heated sulfur-free hydrocarbon stream 115'. In certain aspects, heated sulfur free hydrocarbon stream 115' can be at a temperature of 200° C. to 500° C. and all ranges and values there between including 200° C. to 220° C., 220° C. to 240° C., 240° C. to 260° C., 260° C. to 280° C., 280° C. to 300° C., 300° C. to 320° C., 320° C. to 340° C., 340° C. to 360° C., 360° C. to 380° C., 380° C. to 400° C., 400° C. to 420° C., 420° C. to 440° C., 440° C. to 460° C., 460° C. to 480° C., and 480° C. to 500° C. As shown in block 204, in embodiments of the invention, process 200 can further include combining heated sulfur-free hydrocarbon stream 115' comprising iso-alkanes with sulfur-containing hydrocarbon stream 116 from storage vessel 107 to form reactant feed stream 117. Sulfur-containing hydrocarbon stream 116 contains one or more sulfur-containing compounds described above. A temperature of sulfur-containing hydrocarbon stream 116 can be lower than the temperature of heated sulfur free hydrocarbon stream 115'. In some embodiments, sulfur-containing hydrocarbon stream 116 can be at a temperature of 30° C. to 100° C. and all ranges and values there between including ranges of 30° C. to 35° C., 35 to 40° C., 40° C. to 45° C., 45° C. to 50° C., 50° C. to 55° C., 55° C. to 60° C., 60° C. to 65° C., 65° C. to 70° C., 70° C. to 75° C., 75° C. to 80° C., 80° C. to 85° C., 85° C. to 90° C., 90° C. to 95° C., and 95° C. to 100° C. Overall, sulfur-containing compounds are introduced downstream of heat exchanger 105 (e.g., gas-gas heat exchanger). Thus, the sulfur content in the gas-gas exchanger can be effectively controlled, thereby preventing heat exchanger malfunction caused by high sulfur content in reactant feed stream 117.

In certain aspects, a volumetric ratio of heated sulfur-free hydrocarbon stream 115' to sulfur-containing hydrocarbon stream 116 in the combining at block 204 can be in a range of 5 to 10, or greater than, equal to, or between any two of 5, 6, 7, 8, 9, and 10. Reactant feed stream 117 that includes isobutane can further include sulfur-containing compounds at a concentration of 5 to 100 ppm, preferably 10 to 80 ppm and all ranges and values there between including 5 to 10 ppm, 10 to 15 ppm, 15 to 20 ppm, 20 to 25 ppm, 25 to 30 ppm, 30 to 35 ppm, 35 to 40 ppm, 40 to 45 ppm, 45 to 50 ppm, 50 to 55 ppm, 55 to 60 ppm, 60 to 65 ppm, 65 to 70 ppm, 70 to 75 ppm, 75 to 80 ppm, 80 to 85 ppm, 85 to 90 ppm, 90 to 95 ppm, and 95 to 100 ppm.

Reactant stream 117 can enter dehydrogenation unit 106. As shown in block 205, process 200 can further include contacting reactant feed stream 117 with a dehydrogenation catalyst under conditions sufficient to produce a first product stream comprising iso-alkenes. In some embodiments, the dehydrogenation catalyst can include a supported transition metal (e.g., Column 6 and/or Column 10) catalyst. Non-limiting examples for the dehydrogenation catalyst include an alumina supported chromium catalyst and an alumina supported platinum-tin catalyst. In some embodiments, the dehydrogenation conditions can include a reaction temperature of 550° C. to 600° C. and all ranges and values there between including 550° C. to 555° C., 555° C. to 560° C., 560° C. to 565° C., 565° C. to 570° C., 570° C. to 575° C., 575° C. to 580° C., 580° C. to 585° C., 585° C. to 590° C., 590° C. to 595° C., and 595° C. to 600° C. The dehydrogenation conditions can further include a reaction pressure of about 0.1 MPa. A liquid hourly space velocity of reactant feed stream can be in a range of 200 to 300 $hr^{-1}$ and all ranges and values there between including ranges of 200 to 210 $hr^{-1}$, 210 to 220 $hr^{-1}$, 220 to 230 $hr^{-1}$, 230 to 240 $hr^{-1}$, 240 to 250 $hr^{-1}$, 250 to 260 $hr^{-1}$, 260 to 270 $hr^{-1}$, 270 to 280 $hr^{-1}$, 280 to 290 $hr^{-1}$, and 290 to 300 $hr^{-1}$.

The sulfur containing compounds from reactant feed stream 117 can be configured to resist coke (carbonaceous deposit) formation on the dehydrogenation catalyst, thereby increasing on-stream factor of dehydrogenation unit 106 by about 1 to 10% or any value there between compared to a process that does not feed sulfur containing compounds into dehydrogenation unit 106. Further, the yield of isobutylene from isobutane using process 200 can be about 4% higher than an isobutane dehydrogenation process that does not include feeding sulfur containing compounds to the dehydrogenation unit.

The iso-alkenes formed at block 205 can contain isobutylene. In certain aspects, first product stream 118 can flow through heat exchanger 105 as a working fluid to heat sulfur-free hydrocarbon stream 115 to form heated sulfur-free hydrocarbon stream 115' and cool first product stream 118 to form cooled first product stream 118'. Cooled first product stream 118' can flow to isobutylene storage vessel 108.

In some more particular embodiments, sulfur rich stream 113 can include isobutylene and/or isobutane. At least some sulfur rich stream 113 can form second sulfur containing hydrocarbon stream 124. In certain aspects, an outlet of storage vessel 107 can be in fluid communication with isobutylene storage vessel 108, which is further configured to receive at least some sulfur containing compounds and hydrocarbons contained in second sulfur containing hydrocarbon stream 124 from storage vessel 107.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention can provide functionality as described herein using various blocks in a sequence different than that of FIG. 2.

Figure 3:
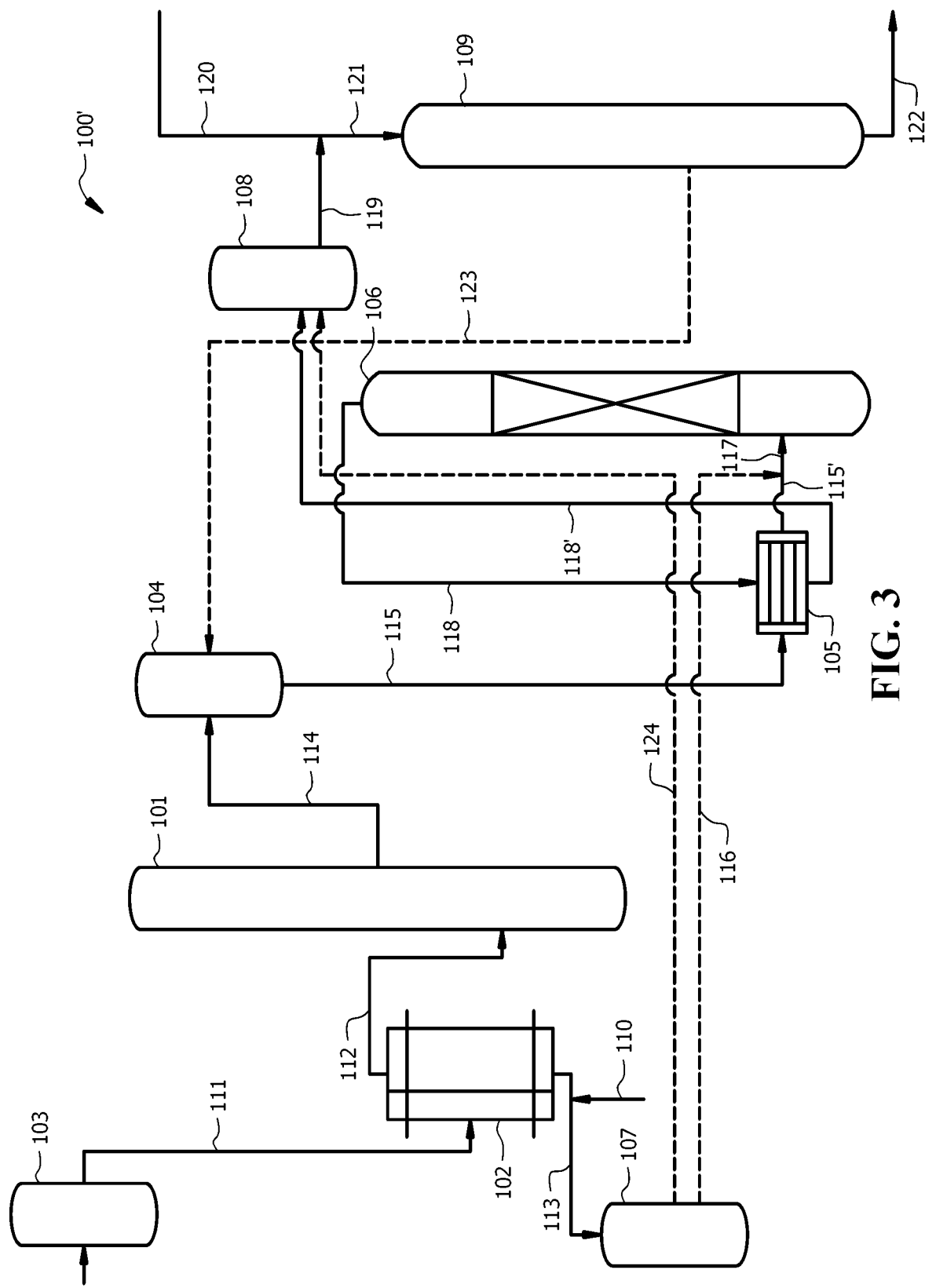
FIG. 3 shows a schematic diagram of a system for producing isobutylene integrated with a MTBE synthesis unit, according to embodiments of the invention.

As shown in FIG. 3, system 100' of producing isobutylene are substantially the same as system 100. In certain aspects, system 100' can include MTBE synthesis unit 109. At least some isobutylene stream 119 containing primarily isobutylene and/or isobutane can flow to MTBE synthesis unit 109 from isobutylene storage vessel 108. In a particular embodiment, a desulfurization unit can be installed downstream to isobutylene storage vessel 108 configured to remove sulfur-containing compounds in isobutylene stream 119. Alternatively, in more particular embodiments, sulfur-containing compounds can be removed separately from cooled first product stream 118' and sulfur-containing hydrocarbon stream 124 to form a desulfurized first product stream and a desulfurized hydrocarbon stream, respectively. The desulfurized first product stream and the desulfurized hydrocarbon stream can combine to form isobutylene stream 119.

Isobutylene stream 119 from the desulfurization unit can join methanol stream 120 to form MTBE feed stream 121 such that MTBE feed stream 121 flowing into MTBE synthesis unit 109 contains no, or substantially no sulfur-containing compounds or less than 10 ppm of sulfur containing compounds. MTBE synthesis unit can include a MTBE reactor and a product separator. The MTBE reactor can be configured to react isobutylene with methanol in the presence of a catalyst to form MTBE in a second product stream. The product separator can be configured to separate the second product stream into MTBE stream 122 that includes primarily MTBE and unreacted product stream 123 that includes unreacted isobutane and/or unreacted isobutylene. In some embodiments, an outlet of the product separator can be in fluid communication with dehydrogenation vessel 104, which is further configured to receive unreacted product stream 123 from the product separator of MTBE synthesis unit 109. As an alternative to, or in addition to dehydrogenation vessel 104, an outlet of the product separator of MTBE synthesis unit 109 can be directly in fluid communication with an inlet of dehydrogenation unit 106, which is further configured to receive and react at least some unreacted isobutane in unreacted product stream 123 to form isobutylene.

As sulfur-containing compounds can be substantially removed from isobutylene stream 119, unreacted product stream 123 can include no, or substantially no sulfur-containing compound. Recycling of unreacted product 123 does not introduce sulfur-containing compounds in sulfur free hydrocarbon stream 115. Therefore, for reactant feed stream 117 feeding into dehydrogenation unit 106, sulfur-containing compounds are introduced downstream to heat exchanger 105 (gas-gas heat exchanger). Thus, the sulfur content in the gas-gas exchanger can be effectively controlled, thereby preventing heat exchanger malfunction caused by high sulfur content in reactant feed stream 117.

In some other embodiments, sulfur-containing compounds in cooled first product stream 118' and/or sulfur-containing hydrocarbon stream 124 are not removed. By way of example, hydrocarbon stream 124 stream can be used when the sulfur level is less than 5 ppm. Therefore, isobutylene stream 119 can include sulfur-containing compounds. The isobutylene of isobutylene stream 119 can react with the methanol in MTBE synthesis unit 109 to form a second product stream containing MTBE, unreacted isobutylene, and isobutane. The second product stream can be separated into MTBE stream 122 containing primarily MTBE and unreacted product stream 123 containing isobutane and/or isobutylene. In certain aspects, unreacted product stream 123 can include sulfur-containing compounds. Unreacted product stream 123 that includes sulfur-containing compounds can be flowed into reactant feed stream 117, which can be subsequently flowed into dehydrogenation unit 106. As an alternative to or in addition to being flowed into reactant feed stream 117, unreacted product stream 123 can be flowed into dehydrogenation feed vessel 104, thereby adding sulfur compounds into sulfur free hydrocarbon stream 115 flowing from dehydrogenation feed vessel 104. Without wishing to be bound by theory, it is believed that as the dehydrogenation temperature increases, the sulfur compounds decompose and form $H_2S$. Hydrogen and hydrogen sulfide react with catalyst metal to convert the oxide into the corresponding metal sulfide. (e.g., $MO+H_2S \Rightarrow MS+H_2O$) during the regeneration step of catalyst the metal sulfide undergoes oxidization back to metal oxide. The formed sulfur oxide can then be removed via a scrubber system (not shown) where it is removed from the system.

The systems and process described herein can also include various equipment that is not shown and is known to one of skill in the art of chemical processing. For example, some controllers, piping, computers, valves, pumps, heaters, thermocouples, pressure indicators, mixers, heat exchangers, and the like may not be shown.

As part of the disclosure of the present invention, specific examples are included below. The examples are for illustrative purposes only and are not intended to limit the invention. Those of ordinary skill in the art will readily recognize parameters that can be changed or modified to yield essentially the same results.

EXAMPLES

Example 1

Effects of Sulfur Containing Compounds on Coke Formation Over a Dehydrogenation Catalyst Experiments were conducted to study the effects of sulfur-containing compounds on coke formation in an alkane dehydrogenation catalyst bed alkane dehydrogenation. In the experiments, a hydrocarbon stream containing isobutane was fed into a dehydrogenation reactor containing a fluidized catalyst bed that contained an alumina supported chromium catalyst. The dehydrogenation reaction of isobutane was performed under a reaction temperature of 580° C., a reaction pressure of 1 atm, and a liquid hourly space velocity of 250 $h^{-1}$.

Both sulfur-free hydrocarbon stream and sulfur-containing hydrocarbon stream were used in the experiments. The sulfur-free hydrocarbon stream contained about 99.9 mol. % isobutane. The sulfur-containing hydrocarbon stream included substantially the same composition as the sulfur-free hydrocarbon stream with 5 to 10 ppm of added sulfur. Table 1 lists the materials used and conditions of the process.

TABLE 1

| | |
|---|---|
| Feed | Isobutane 99.9% (5-80 ppm sulfur-$H_2S$) |
| Dehydrogenation Catalyst | Chromia Alumina |
| Reactor type | Isothermal Fluidization Bed Reactor |
| Space Velocity | 250 hour$^{-1}$ |
| Pressure | Atmospheric |
| Dehydrogenation temperature | 590° C. Time on stream 5 min |
| Regeneration temperature | 650° C. |
| Reduction temperature | 650° C. |

Figure 4:
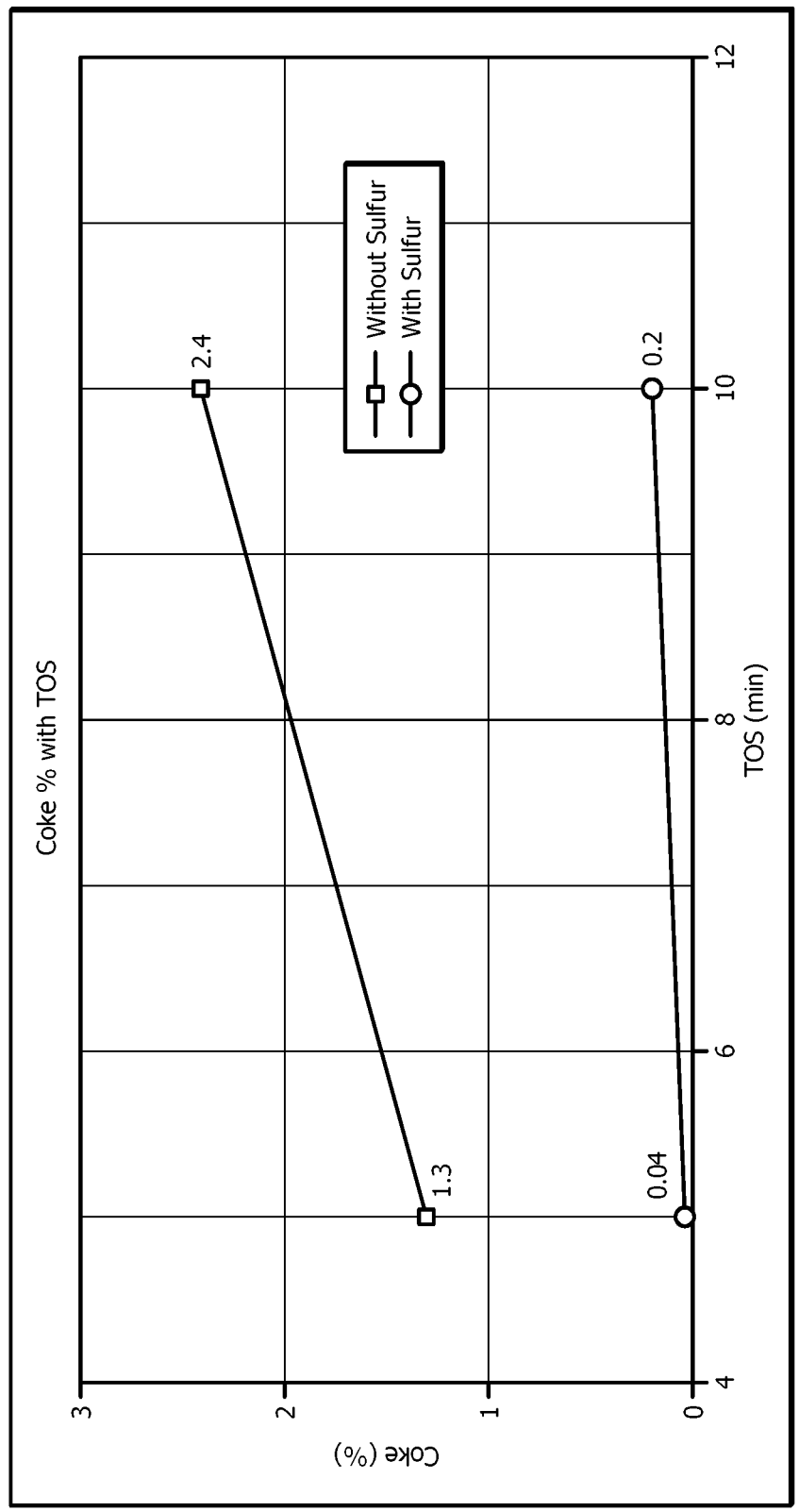
FIG. 4 shows results of coke formation on catalyst of fluidized catalyst bed during an alkane dehydrogenation process with and without sulfur injection.

Coke formation in the catalyst was determined at 5 minutes and 10 minutes (time on-stream) of the dehydrogenation process. The results of using sulfur-free hydrocarbon stream and sulfur-containing hydrocarbon stream were compared and shown in FIG. 4. FIG. 4 indicates that at 5 minutes on-stream, about 0.04% when sulfur-containing compounds were included in the hydrocarbon stream as compared to 1.3% without sulfur containing compounds. Similarly, at 10 minutes on stream about 0.2% when sulfur-containing compounds were included in the hydrocarbon stream as compared to 2.4% with sulfur-containing compounds. Therefore, the results confirm that the presence of sulfur decreases the formation of coke.

The coke was analyzed by carbon sulfur analyzer using a combustion method and Thermogravimetric analysis (TGA) using a carbon analyzer detector. The amount of Coke was related to catalyst activity in turn leading to deactivation which is caused by (i) a decrease of the number of active sites; (ii) a decrease of the quality of the active sites; and (iii) a degradation in accessibility of the pore space.)

Figure 5A:
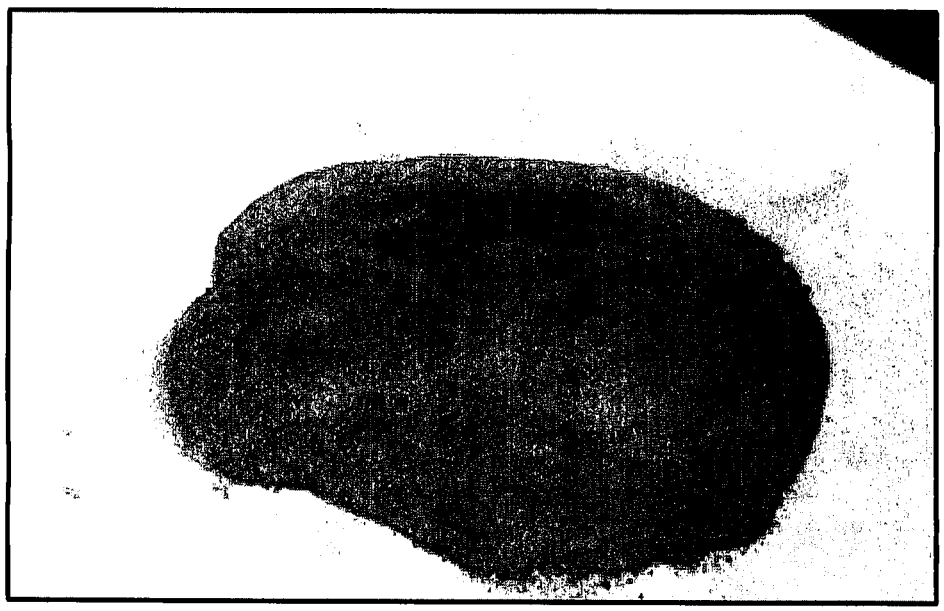
FIGS. 5A and 5B show coke formation on a catalyst after an alkane dehydrogenation process with (FIG. 5A) and without (FIG. 5B) sulfur injection to the hydrocarbon feed stream.
Figure 5B:
Figure 6:
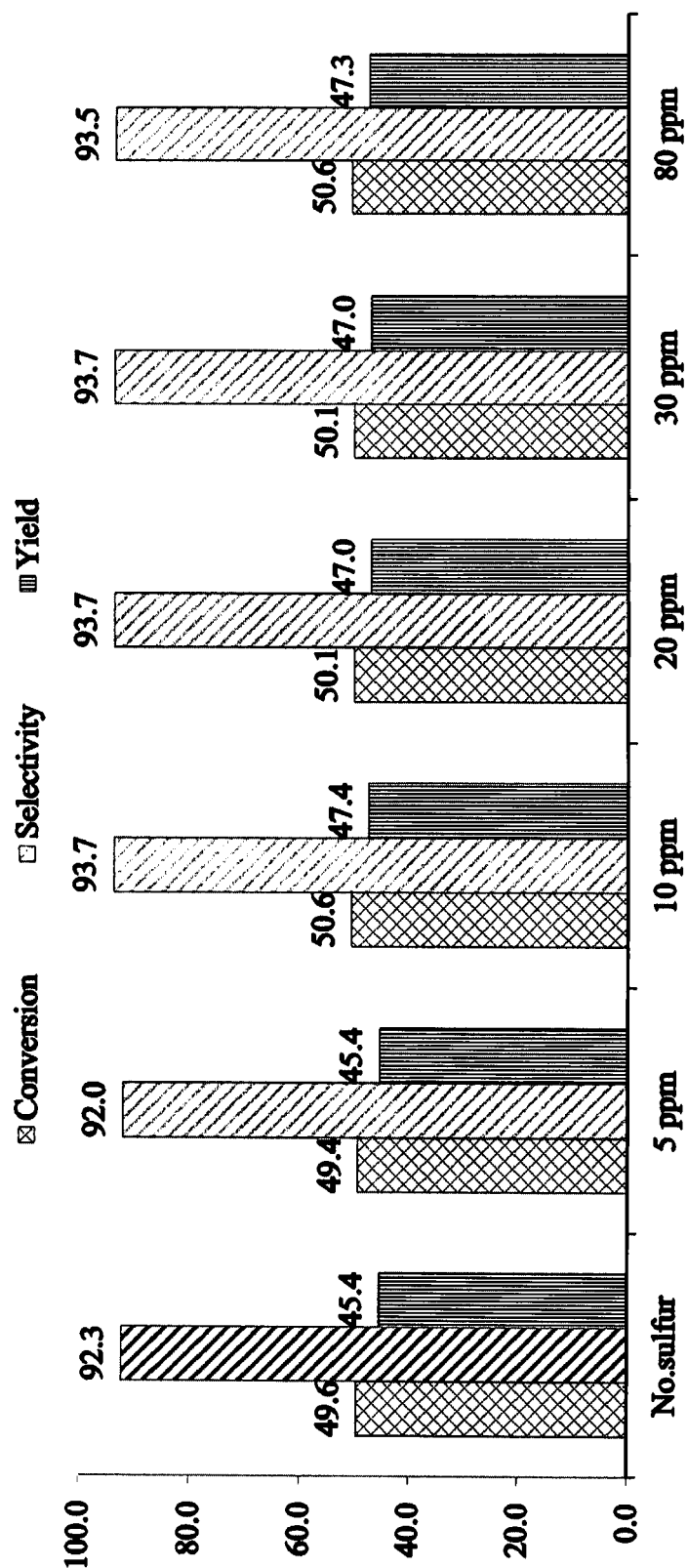
FIG. 6 shows conversion, selectivity, and yield for an alkane dehydrogenation process without and with 5, 10, 20, 30 and 80 ppm of sulfur injection to the hydrocarbon feed stream.

The dehydrogenation of isobutane was also performed under a reaction temperature of 590° C., a reaction pressure of 1 atm, and a liquid hourly space velocity of 250 h$^{-1}$. Both sulfur free hydrocarbon stream and sulfur-containing hydrocarbon stream were used as the feed streams for the dehydrogenation process. The sulfur-free hydrocarbon stream contained about 99.9 mol. % isobutane. The sulfur-containing hydrocarbon stream contained substantially the same composition as sulfur-free hydrocarbon stream with 5 to 80 ppm added sulfur as $H_2S$. After 10 cycles of dehydrogenation with 5 minutes of time on-stream, the catalysts from the fluidized catalyst beds used for both feed streams were sampled. The appearances of the catalysts used for dehydrogenating the two types of feed streams (sulfur-free and sulfur-containing hydrocarbon streams) were compared. As shown in FIGS. 5A and 5B, the catalyst used for dehydrogenating sulfur-free hydrocarbons appeared darker in color and more agglomerated than the catalyst used for dehydrogenating sulfur-containing hydrocarbons, indicating more coke formation for the catalyst used for dehydrogenating sulfur-free hydrocarbons. Therefore, from the results in FIGS. 5A and 5B it was determined that sulfur can resist and/or reduce coke formation on the dehydrogenation catalyst. FIG. 6 shows the catalyst activity performance. From the data in FIG. 6 is was determined that the sulfur content increased to greater than 10 ppm, the selectivity, conversion and yield increased as compared to streams without sulfur.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein can be utilized. Accordingly, the appended claims are intended to include within their scope such processes, machines, manufacture, compositions of matter, means, methods, or steps.

The invention claimed is:

1. An alkane dehydrogenation process, the process comprising:
    combining a sulfur-free hydrocarbon stream comprising alkanes with a sulfur-containing hydrocarbon stream comprising a sulfur-containing compound and hydrocarbons to form a reactant feed stream, wherein the temperature of the sulfur-free hydrocarbon stream is greater than the sulfur-containing hydrocarbon stream; and
    contacting the reactant feed stream with a dehydrogenation catalyst under conditions sufficient to produce a first product stream comprising alkenes.

2. The process of claim 1, further comprising passing the sulfur-free stream through a heat exchanger to increase the temperature of the sulfur-free hydrocarbon stream before combining the sulfur-free hydrocarbon stream with the sulfur containing hydrocarbon stream.

3. The process of claim 1, wherein the alkanes include isobutane, and the iso-alkenes of the first product stream include isobutylene.

4. The process of claim 1, wherein the sulfur-free hydrocarbon stream and the sulfur containing hydrocarbon stream each contain n-butane, 1-butene, 2-butene, or a combinations thereof.

5. The process of claim 1, wherein the reactant feed stream comprises isobutane and the sulfur-containing compound having a concentration of 5 ppm to 100 ppm.

6. The process of claim 1, wherein the hydrocarbons of sulfur containing hydrocarbon stream further comprises isobutylene and/or isobutane.

7. The process of claim 6, further comprising:
    removing the sulfur-containing compounds from the sulfur containing hydrocarbon stream and the first product stream to form a desulfurized hydrocarbon stream and a desulfurized first product stream respectively;
    contacting, at least some of the isobutane of the desulfurized hydrocarbon stream and/or, at least some, isobutylene of the desulfurized first product stream with methanol to produce a second product stream comprising methyl tert-butyl ether and an unreacted product stream comprising isobutylene and isobutane; and
    recycling, at least some of, the unreacted product stream into the sulfur free hydrocarbon stream and/or reactant feed stream.

8. The process of claim 1, wherein the sulfur-free hydrocarbon stream is heated in a heat exchanger by a working fluid containing the product stream that comprises iso-alkene.

9. The process of claim 1, wherein the sulfur containing hydrocarbon stream has a temperature in a range of 30° C. to 100° C., and the sulfur-free stream has a temperature in a range of 200° C. to 500° C.

10. The process of claim 1, wherein, in the reactant feed stream, the sulfur free stream has a sulfur content of less than 10 ppm, preferably less than 5 ppm.

11. The process of claim 1, the sulfur containing compound comprise one or more organic sulfides, one or more organic disulfides, one or more organic polysulfides, or combinations thereof.

12. The process of claim 11, wherein the one or more sulfides have a formula of $R_1-(S)_n-R_2$, where n is 1 or 2, and $R_1$ and $R_2$ are each individually a hydrogen or an alkyl group.

13. The process of claim 11, wherein the one or more disulfides have a formula of $R_3-S-R_4-S-R_5$, where $R_3$ and $R_5$ are each individually a hydrogen atom or an alkyl group, and $R_4$ is an alkyl group bound to two sulfur atoms.

14. The process of claim 1, wherein the conditions sufficient to produce the first product stream include a reaction temperature in a range of 550° C. to 600° C., and a reaction pressure of about 0.1 MPa.

15. The process of claim 1, wherein the conditions sufficient to produce the first product stream include a liquid hourly space velocity of 200 $hr^{-1}$ to 300 $hr^{-1}$.

16. The process of claim 1, wherein the process is performed in a continuous mode.

17. The process of claim 1, wherein the dehydrogenation catalyst include chromium oxide supported on alumina.

18. The process of claim 17, wherein the dehydrogenation catalyst is contained in a fluidized bed.

19. The process of claim 1, wherein the sulfur-containing hydrocarbon stream is formed by adding the sulfur-containing compounds into a $C_4$ stream.

20. A process for producing isobutylene, the process comprising:
    (a) combining a sulfur-free hydrocarbon stream comprising isobutane with a sulfur containing hydrocarbon stream comprising isobutane to form a reactant feed stream; and contacting the reactant feed stream with a dehydrogenation catalyst under conditions sufficient to produce a product stream comprising isobutylene;
    (b) optionally separating the isobutylene from the product stream of step (a);
    (c) contacting the product stream comprising isobutylene from step (a) and or isobutylene from step (b) with methanol to produce a product stream comprising methyl tert-butyl ether and an unreacted product stream comprising isobutane; and
    (d) contacting the unreacted product stream comprising isobutane with the dehydrogenation catalyst under conditions sufficient to convert the isobutane to isobutylene and produce an isobutylene product stream.

* * * * *